United States Patent
Mai et al.

(10) Patent No.: US 6,643,548 B1
(45) Date of Patent: Nov. 4, 2003

(54) IMPLANTABLE CARDIAC STIMULATION DEVICE FOR MONITORING HEART SOUNDS TO DETECT PROGRESSION AND REGRESSION OF HEART DISEASE AND METHOD THEREOF

(75) Inventors: Junyu Mai, Valencia, CA (US); Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/544,596

(22) Filed: Apr. 6, 2000

(51) Int. Cl.$^7$ .................................................. A61N 1/08
(52) U.S. Cl. .............................. 607/17; 607/18; 607/6; 600/513; 600/514; 600/528
(58) Field of Search .................... 600/374, 509, 600/513, 514, 515, 516, 517, 518, 519, 521, 528; 607/4, 5, 7, 9, 11, 14, 17, 18, 19, 25, 62, 119

(56) References Cited

U.S. PATENT DOCUMENTS

| | | | | |
|---|---|---|---|---|
| 4,830,006 A | * | 5/1989 | Haluska et al. | 128/419 PG |
| 4,905,706 A | * | 3/1990 | Duff et al. | 128/701 |
| 5,012,815 A | * | 5/1991 | Bennett, Jr. et al. | 128/715 |
| 5,466,254 A | | 11/1995 | Helland | 607/123 |
| 5,476,483 A | | 12/1995 | Bornzin et al. | 607/17 |
| 5,554,177 A | * | 9/1996 | Kieval et al. | 607/17 |
| 5,687,738 A | * | 11/1997 | Shapiro et al. | 128/715 |
| 5,700,283 A | * | 12/1997 | Salo | 607/17 |
| 6,044,298 A | * | 3/2000 | Salo | 607/17 |
| 6,190,324 B1 | * | 2/2001 | Kieval et al. | 600/483 |
| 6,409,675 B1 | * | 6/2002 | Turcott | 600/508 |
| 6,411,840 B1 | * | 6/2002 | Bardy | 600/513 |

OTHER PUBLICATIONS

R.J. Lehner, et al "*A Three–Channel Microcomputer System for Segmentation and Characterization of the Phonocardiogram,*" pp. 485–489, IEEE Transactions on Biomedical Engineering, vol. BME–34, No. 6, (6–87).

G. Jamous, et al "*Optimal Time–Window Duration for Computing Time/Frequency Representations of Normal Phonocardiograms in Dogs,*" pp. 503–508, Medical & Biological Engineering & Computing (1992).

M.S. Obaidat *Phonocardiogram Signal Analysis: Techniques and Performance Comparison*, pp. 221–227, Journal of Medical Engineering & Technology, vol. 17, No. 6 (1993).

H.L. Baranek, et al "*Automatic Detection of Sounds and Murmurs in Patients with Ionescu–Shiley Aortic Bioprostheses,*" pp. 449–455, Medical & Biological Engineering & Computing (9/89).

D. Smith, B.M.E., et al "*Chest Wall Velocity and the Second Heart Sound, an Improved Sensor of S2 Splitting,*" pp. 1304–1311, Circulation, vol. 67, No. 6 (Jun. 1983).

* cited by examiner

Primary Examiner—Jeffrey R. Jastrzab
Assistant Examiner—Frances P. Oropeza

(57) ABSTRACT

A system and method for use in an implantable cardiac device permits the monitoring of progression and regression in heart disease, such as congestive heart failure. During a monitoring period, a sensing circuit produces an electrogram signal of the patient's heart and a sound sensor produces a phonocardiogram of the patient's heart. A processor determines a predetermined characteristic of the heart sounds, such as amplitude, time intervals between selected heart sounds, and time intervals between selected heart sound and selected electrogram features for each cardiac cycle occurring during a monitoring period. The predetermined characteristics are thereafter averaged and stored in a memory for later retrieval. Relative changes in the average time intervals over time provides an indication of the progression or regression of the heart disease.

41 Claims, 4 Drawing Sheets

IMPLANTABLE CARDIAC STIMULATION DEVICE FOR MONITORING HEART SOUNDS TO DETECT PROGRESSION AND REGRESSION OF HEART DISEASE AND METHOD THEREOF

FIELD OF THE INVENTION

The present invention is generally directed to an implantable device for monitoring the progression or regression of heart disease. The present invention is more particularly directed to such a device which identifies heart sounds and electrogram features from heart sound and electrogram signals representing emitted sound and electrical activity of a patient's heart and determines time intervals between selected heart sounds and electrogram features indicative of the progression or regression of the heart disease.

BACKGROUND OF THE INVENTION

More people die of heart disease than any other single cause. One common form of heart disease is congestive heart failure.

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy, have a poor prognosis and limited exercise tolerance. Cardiac pacing has been proposed as a new primary treatment for patients with drug-refractory CHF.

By tracking the progression or regression of heart disease, such as CHF, more closely, treatments could be managed more effectively. Commonly, patients with heart disease have an implanted cardiac stimulation device. Hence, it would be advantageous if the implanted cardiac stimulation device were able to aid in the tracking of the progression or regression of the heart disease. While some devices have been proposed to track a patient's heart condition, these devices have relied upon sensing activity and/or respiration of the patient. Unfortunately, this requires additional complexity to an already complex device. The present invention addresses the issues of tracking heart disease progression or regression by making use of existing circuitry commonly available in implantable cardiac stimulation devices.

SUMMARY OF THE INVENTION

The present invention provides a system and method, for use in an implantable cardiac device, for monitoring a predetermined characteristic of heart sound to determine the progression or regression in heart disease, such as congestive heart failure.

A sensing circuit produces an electrogram signal indicative of the electrical activity of the patient's heart. A sound, or acoustic, sensor produces a phonocardiogram representing the sounds omitted from the patient's heart. A processor determines time intervals between selected heart sounds in the phonocardiogram and morphological features in electrogram. Relative changes in the time intervals or the amplitude, over time, are indicative of progression or regression in the heart disease. The time intervals and/or amplitudes are stored in a memory for later telemetry to an external receiver for review by medical personnel.

The determined time intervals may be time intervals between a heart sound and a morphological feature of a common cardiac cycle, such as an R-wave. The time intervals may alternatively or further be time intervals between different heart sounds of a common cardiac cycle.

The time intervals may more specifically be time spans between an R wave and an S1 heart sound and time spans between an S1 heart sound and an S2 heart sound. Also, the presence of an S3 heart sound may be indicative of elevated left ventricular diastolic pressure, as occurs in CHF patients. The presence of an S4 heart sound has been found to be indicative of hypertension, hypertrophic cardiomyopathy, cardiomyopathies, ischemia and/or myocardial infarction.

The time intervals and/or amplitudes are preferably determined for each cardiac cycle occurring over a time period, once each day, when the rhythm is being stable such as when the patient is at rest. The time intervals and/or amplitudes are then preferably averaged and the average time intervals stored in memory for later retrieval.

An increase in either time interval, over time, may be indicative of a progression in the heart disease. Conversely, a decrease in the time intervals may be indicative of a regression in the heart disease. To assure consistent data collection, the time intervals are preferably determined from heart activity while the patient is at rest and the cardiac signals are stable.

In accordance with a further aspect of the present invention, when the device is a cardiac stimulation device for delivering therapy, such as pacing therapy to the patient's heart, the device itself may adjust stimulation therapy responsive to the determined physiological parameter measurements. The stimulation therapy adjustment may take the form, for example, of pacing rate adjustments to assist the patient in breathing or in the removal of fluid from the lungs.

BRIEF DESCRIPTION OF THE DRAWINGS

The above and other aspects, features, and advantages of the present invention will be more apparent from the following more particular description thereof presented in conjunction with the following drawings and wherein.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
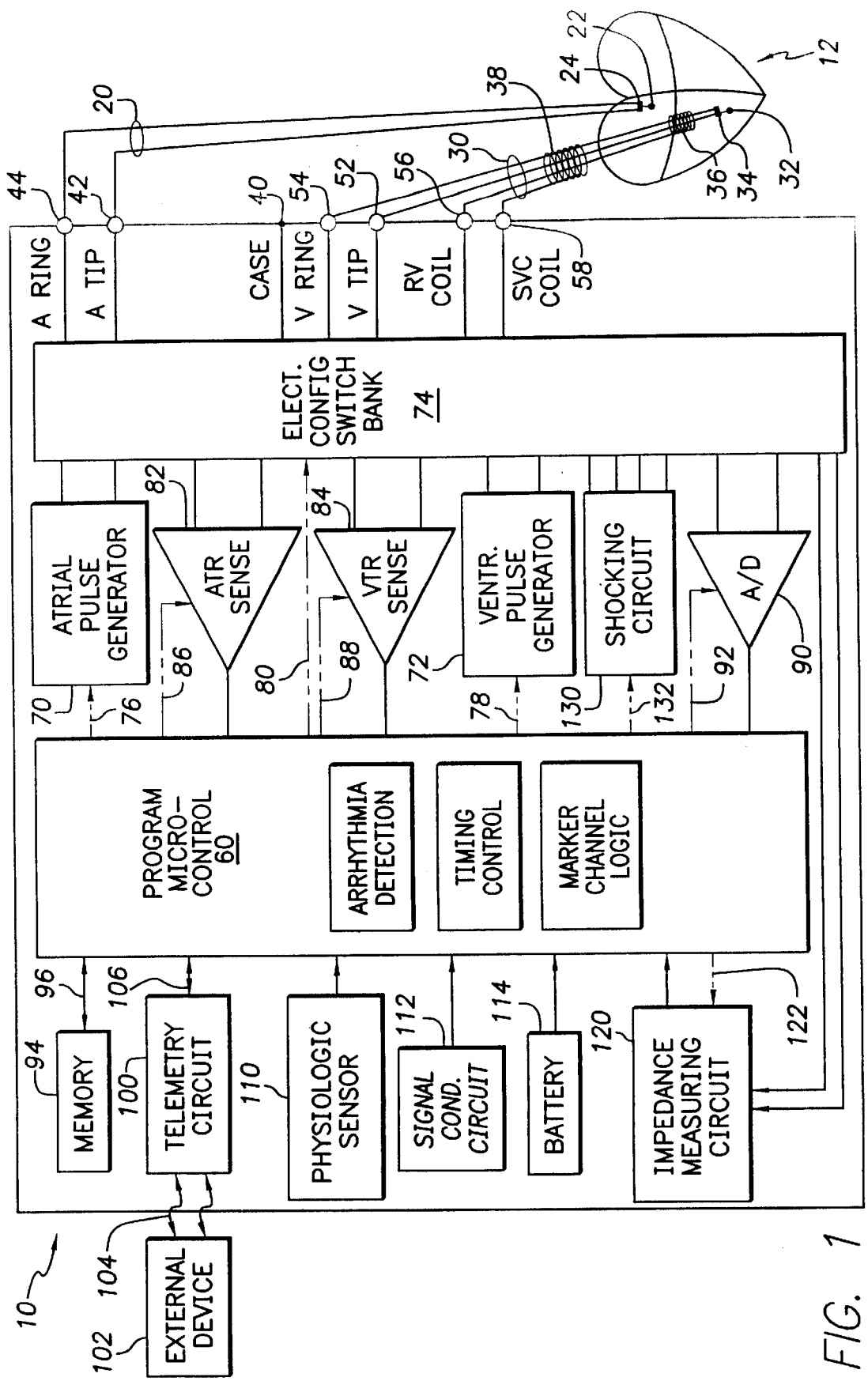
FIG. 1 shows a simplified functional block diagram of a combined implantable cardioverter/defibrillator and pacemaker (ICD), which represents one type of implantable stimulation device with which the present invention may be used.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/457,277, "A Self-Anchoring, Steerable Coronary Sinus Lead" (Pianca et al.), which is a continuation-in-part of 09/196,898, "A Self-Anchoring Coronary Sinus Lead" (Pianca et. al), now abandoned; and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the device 10 utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to sense or acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes. As will be seen subsequently, the data acquisition system 90 may be utilized to provide an electrogram (EGM) signal for use in monitoring the progression or regression in heart disease in accordance with the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy. Further, the memory 94 stores electrogram data from the data acquisition system, which electrogram data may then be used for subsequent analysis for monitoring the progression or regression in heart disease in accordance with the present invention.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms, status information relating to the operation of the device 10 (as contained in the microcontroller 60 or memory 94), and heart disease monitoring results to be sent to the external device 102 through the established communication link 104.

The stimulation device 10 further includes a physiologic sensor 110. Such sensors are commonly called "rate-responsive" sensors. The physiological sensor 110 is used to detect and generate a raw signal representing the activity of the patient, to which the microcontroller 60 responds by adjusting the rate and AV Delay at which the atrial and ventricular pulse generators, 70 and 72, generate stimulation pulses.

The activity sensor 110 is preferably an accelerometer or a piezoelectric crystal, which is mounted within the housing 40 of the stimulation device 10. The sensor is further preferably more sensitive than those more commonly used in implantable stimulation devices and preferably has a sensitivity of, for example, 1 MG/MV. This not only permits the sensor 110 to be used for sensing activity or exercise state of the patient, but in addition, with signal conditioning provided by a signal conditioning circuit 112, it may be used to sense sounds emitted from the patient's heart to provide a phonocardiogram or heart sound signal in accordance with the present invention.

The signal conditioning circuit 112 includes a band pass filter which filters the raw heart sound signal from 10 Hz to 150 Hz. The circuit 112 further includes a rectifier which rectifies the filtered signal and an analog to digital converter which digitizes the filtered and rectified signal before it is provided to the processor for storage in memory 94. Once stored in memory 94, the heart sound signal and electrogram signal are used to monitor the progression or regression of the heart disease in a manner to be described subsequently.

The raw activity sensor signal is still further utilized to determine if the patient is inactive or at rest. This is preferably carried out to permit the electrogram signal and heart sound signal to be utilized for heart disease progression or regression monitoring for only cardiac activity occurring while the patient is at rest to assure consistent data collection and analysis comparison. To that end, both the current activity and an activity variance should be very low. A method of determining activity variable is described in detail in U.S. Pat. No. 5,476,483 which patent is incorporated herein by reference in its entirety.

The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the device 10 may employ lithium/silver vanadium oxide batteries, as is true for many such devices to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 1, the present invention preferably includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that to any desired electrode may be used. The impedance measuring circuit 120 is not critical to the present invention and is shown only for completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
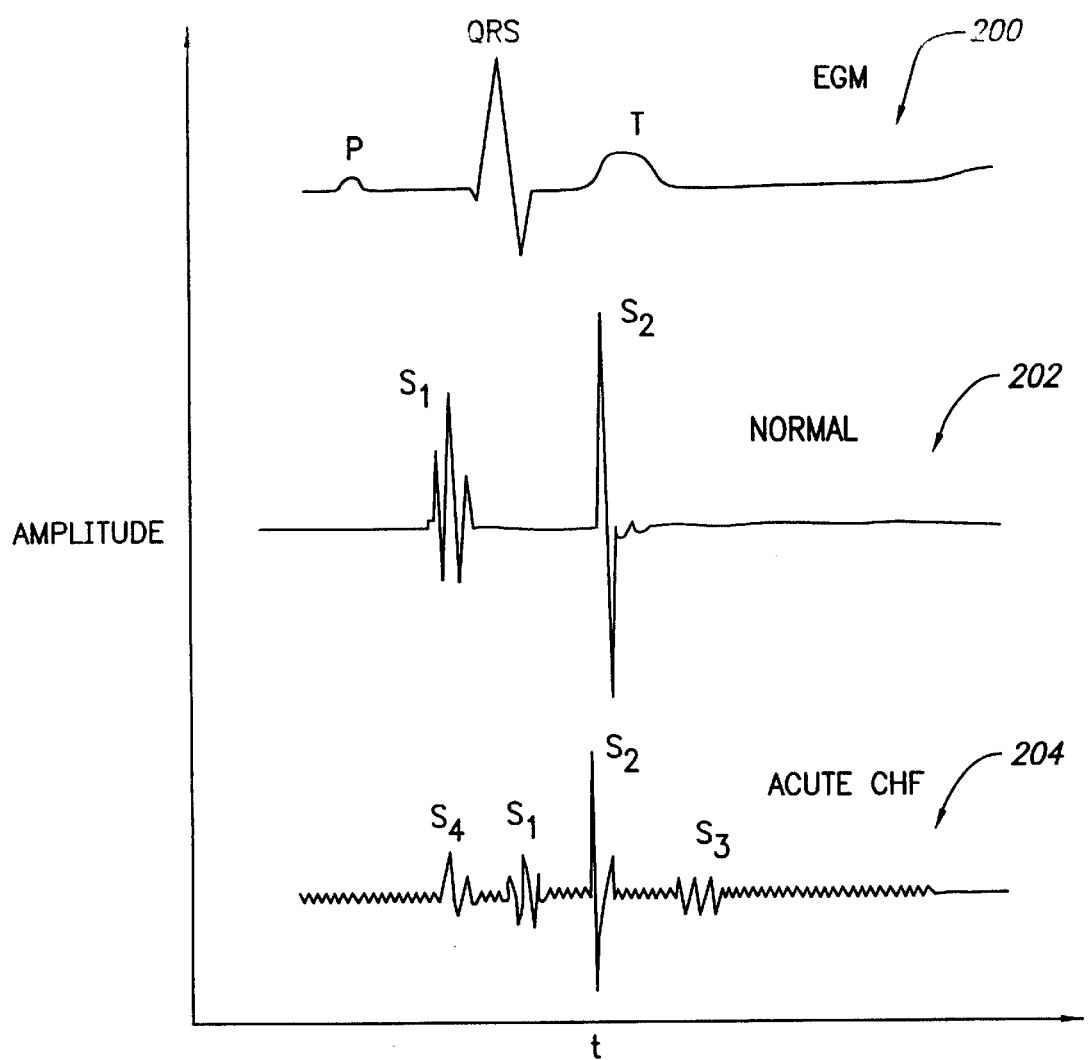
FIG. 2 illustrates a patient's electrogram along with phonocardiograms representative of a normal heart and a heart suffering from congestive heart failure.

FIG. 2 illustrates a patient's EGM 200, a normal heart sound signal or phonocardiogram 202 corresponding to the cardiac cycle of the EGM 200, and a phonocardiogram 204 of a patient suffering from congestive heart failure. The phonocardiogram 204 also corresponds in time relation to the EGM 200.

Turning first to the phonocardiogram 202, in a normal phonocardiogram, for each cardiac cycle, there are two heart sounds, S1 and S2. S1 occurs at the onset of ventricular contraction and corresponds in timing to the QRS complex of the EGM and just precedes a palpable carotid pulse. Its intensity directly relates to the force of ventricular contraction and the amount of ventricular pressure developed during systole. The time interval between the R wave of the QRS complex and S1 is closely related to the pre-ejection period.

The second heart sound, S2, occurs with the end of ventricular systole. It is associated with closure of the aortic and pulmonic valves. Its intensity is directly related to the amount of closing pressure in the aorta and pulmonary arteries.

With a heart suffering from congestive heart failure, as illustrated by the phonocardiogram 204, the amplitude and energy of S1 is decreased. This is due to the decreased cardiac contractility associated with congestive heart failure and hence, decreased force with which the ventricles contract and decreased ventricular pressure. Also, since the time interval from the R wave to S1 is closely related to the pre-ejection period, this time interval increases as congestive heart failure progresses because of the enlargement of the ventricles associated with congestive heart failure.

Also with a heart suffering from congestive heart failure, the amplitude and energy of S2 increases. This is caused by increased atrial blood pressure which increases the force in which the pulmonic and aortic valves close. The time interval from S1 to S2 is closely related to the ejection time. This time interval or duration also increases with a progression of congestive heart failure due to enlargement of the ventricles.

Heart sounds S3 and S4 also exist in a healthy heart, but are very weak. They are more pronounced in CHF patients, and may also by used to indicate the progression and regression of heart disease. The third heart sound, S3, is caused by vibrations occurring during rapid, passive ventricular filling. This is related to the slowed left ventricular isovolumetric relaxation and reduces blood flow velocity into the ventricles. It may be heard in patients with hypertrophic cardiomyopathy and frequently indicates elevated left ventricular diastolic pressure, as occurs in patients with congestive heart failure.

The fourth heart sound, S4, is produced by the end of diastole, when the ventricles are nearly full and atrial contraction further stretches., and fills the ventricles. S4 is the vibrations caused by this filling. S4 may be heard in patients with hypertension, hypertrophic cardiomyopathy, cardiomyopathies, ischemic heart disease, and during or after an acute myocardial infarction.

Except for the occasional brief S3 and S4, diastole is normally silent. When diastolic murmurs occur, they are heard between S2 and S1 corresponding to the interval between the end of the T wave and the beginning of the QRS complex in the electrogram. Diastolic murmurs include aortic regurgitation murmurs, pulmonic regurgitation murmurs and mitral stenosis murmurs, etc.

In accordance with the present invention, at substantially periodic intervals, for example, every day, the R to S1 and S1 to S2 time intervals are determined and averaged over a monitoring period. The monitoring period may be on the order of one minute and may be of longer duration as, for example, five minutes. The average R to S1 and average S1 to S2 time intervals are then stored in memory for later telemetric retrieval. By noting relative changes in the average R to S1 and S1 to S2 time intervals over time, the progression or regression of congestive heart failure may be monitored.

Figure 3:
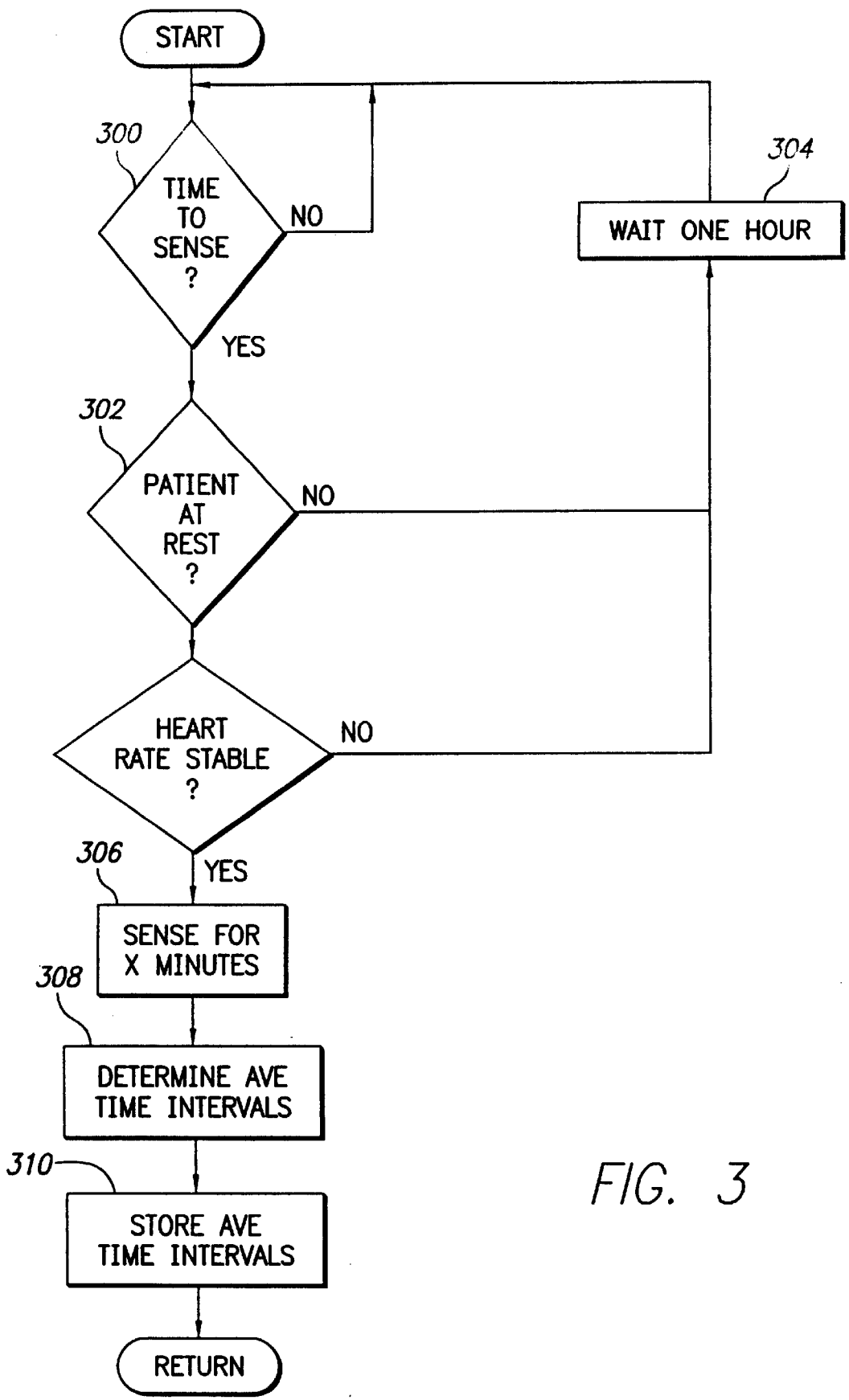
FIG. 3 is a flowchart that illustrates an overview of a method embodying the invention for monitoring a progression or regression of heart disease.

In FIG. 3, a flow chart is shown describing an overview of the operation of the novel features of the present invention. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the monitoring of the progression or regression of the heart disease. Those skilled in the art may readily write such a control program based on the flow charts and other descriptions presented herein.

The overall process illustrated in FIG. 3 initiates with decision block 300 wherein the processor 60 determines if it is time to sense electrogram and heart sound signals to initiate a monitoring period. If it is time to initiate such a monitoring period, the process advances to decision block 302 wherein the processor determines if the patient is at rest. As previously mentioned, the processor may determine if the patient is at rest by noting if the activity and activity variance of the patient is low. Also as previously mentioned, the activity and activity variance may be determined as fully described in U.S. Pat. No. 5,476,483 which is incorporated herein by reference in its entirety.

If the processor determines in decision block 302 that the patient is not at rest, the process then advances to activity block 304 wherein the processor will wait for a fixed period of time, such as one hour. Following the fixed period of time, the process then returns to decision block 300.

Once the patient is detected to be at rest, the process (optionally) advances to block 305 where the processor determines whether the heart rate is stable, for example, by determining if the averaged heart rate is lower than a preset threshold, such as 80 bpm. If it is not stable, the process then advances to block 304 wherein the processor will wait for a fixed period of time, such as one hour. Following the fixed period of time, the process then returns to decision block 300.

If the patient's heart is stable, then the process then advances to activity block 306 wherein the electrogram and heart sound signals are sensed for a fixed period of time as, for example, on the order of one minute. Once the electrogram signal and heart sound signal have been sensed for the fixed period of time, the process then advances to activity block 308 wherein the R to S1 and S1 to S2 time intervals are determined for each cardiac cycle occurring during the monitoring period and then averaged. When activity block 308 is completed, the process then advances to activity block 310 wherein the average R to S1 time interval and the average S1 to S2 time interval are stored in memory for later telemetric retrieval. The process then returns.

Figure 4:
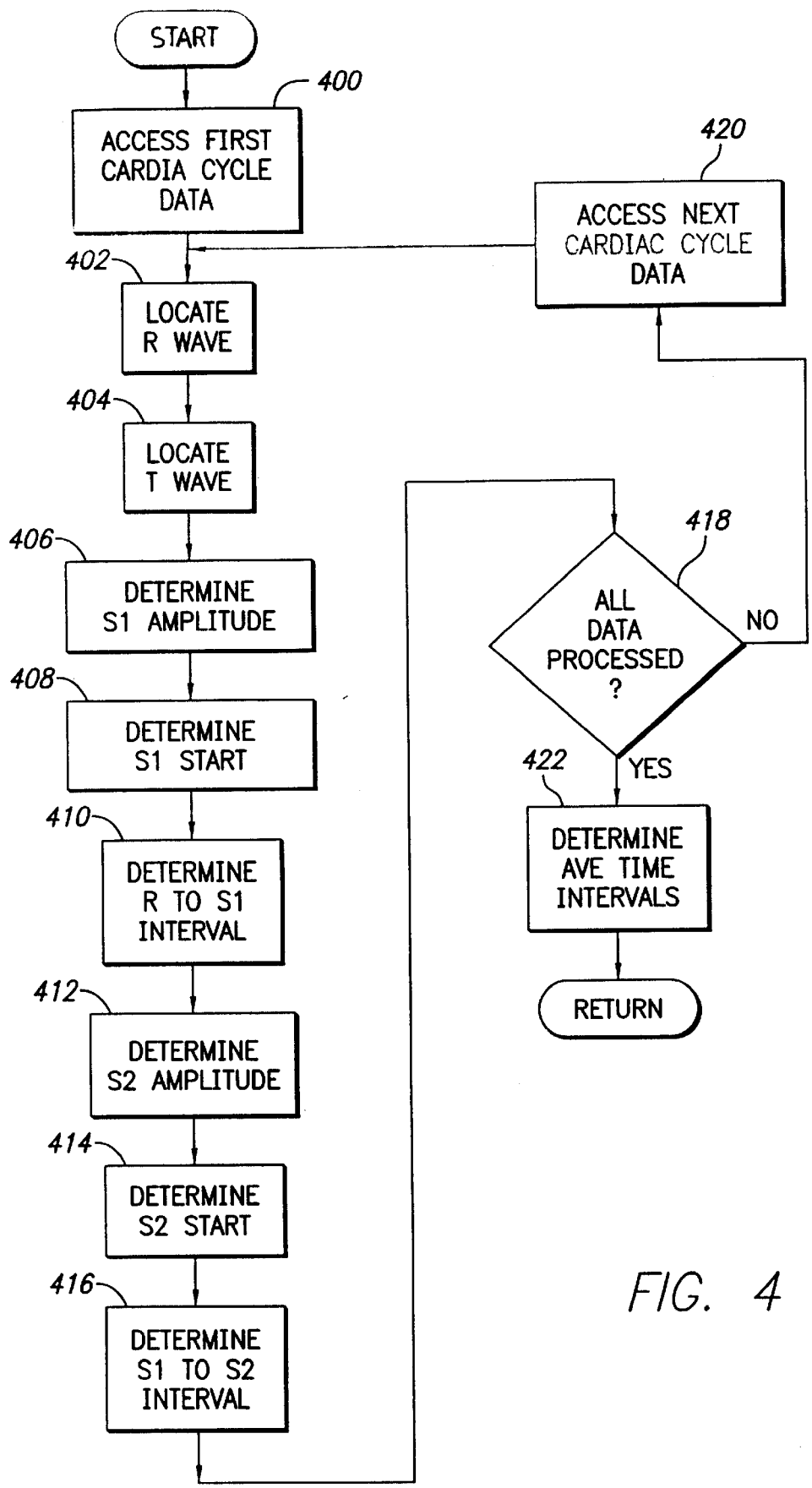
FIG. 4 is a flowchart that illustrates a method used to determine average time intervals from heart sounds and electrogram features in accordance with a preferred embodiment of the present invention.

FIG. 4 illustrates in greater detail the routine which may be utilized by the processor in implementing activity block 308 of FIG. 3. The routine initiates at an activity block 400 wherein the processor accesses the electrogram and heart sound signal data for the first cardiac cycle occurring during the monitoring period. When activity block 400 is completed, the process then advances to activity block 402 wherein the R wave is located. The R wave may be located by determining the maximum of the EGM signal over the complete cardiac cycle. When the R wave is located, the process advances to activity block 404 wherein the T wave is located. In accordance with this preferred embodiment, the T wave may be located by determining the maximum of the electrogram signal from the R wave location plus 100 milliseconds to 100 milliseconds before the next R wave location.

When the T wave is located in accordance with activity block 404, the process advances to activity block 406 wherein the amplitude of the first heart sound (S1) is determined. The amplitude of S1 may be determined by determining the maximum of the heart sound signal between the located R wave and the located T wave. After the amplitude of S1 is determined, the process advances to activity block 408 wherein the start of S1 is determined. The start of S1 may be determined by determining the point in which S1 first achieves 40% of the S1 amplitude determined in activity block 406 following the R wave location.

After the start of S1 is determined in accordance with activity block 408, the process advances to activity block 410 wherein the R to S1 interval is determined. The R to S1 duration may be determined from the duration from the R wave location determined in activity block 402 to the start of S1 determined in activity block 408. The R to S1 time interval may at this time be stored in memory.

Following activity block 410, the process advances to activity block 412 wherein the amplitude of S2 is determined. The amplitude of S2 may be determined by determining the maximum of the heart sound signal during a time period beginning with the T wave location determined in activity block 404 and ending 200 milliseconds thereafter. After the amplitude of S2 is determined in accordance with activity block 414, the process advances to activity block 414 wherein the start of S2 is determined. The start of S2 may be determined in accordance with this preferred embodiment by determining where the heart sound signal first reaches 60% of the S2 amplitude determined in activity block 412 following the T wave location determined in activity block 404. Once the start of S2 is determined in accordance with activity block 414, the process advances to activity block 416 where the time interval between S1 and S2 is determined. The S1 to S2 duration may be determined from determining the time difference between the start of S1 determined in activity block 408 and the start of S2 determined in activity block 414. The S1 to S2 interval may then be stored in memory.

Once activity block 416 is completed, the process advances to a decision block 418 where the processor determines if all of the electrogram and heart sound signal data has been processed. If all of the electrogram and heart sound signal data acquired during the monitoring period has not been processed, the process then advances to activity block 420 wherein the electrogram and heart sound signal data for the next cardiac cycle is accessed by the processor. The process then advances to activity block 402.

If all of the electrogram and heart sound signal data acquired during the monitoring period has been processed as determined in decision block 418, the process then advances to activity block 422 wherein the time intervals are averaged. More specifically, in accordance with activity block 422, the R to S1 intervals determined for the cardiac cycles occurring during the monitoring period are averaged. Similarly, the S1 to S2 time intervals determined for the cardiac cycles occurring during the monitoring period are also averaged. When the R to S1 and S1 and S2 time intervals are averaged, the average R to S1 and average S1 to S2 time intervals may then be stored in memory for later telemetric retrieval. Upon completion of activity block 422, the process returns.

Whenever a physician wishes to review the heart sound measurements, the external programmer 102 may be used to interrogate the implanted cardiac device 10. The telemetry circuitry 100 addresses the memory 94, acquires the heart sound measurements recorded during the extended period of 24 weeks, for example, and transmits the measurements to the external programmer 102 for display. Upon display, the physician will be able to review the activity and respiration measurements to discern the progression of the patient's heart disease, such as congestive heart failure.

For example, if the measurements of heart sound values indicate a decreasing trend, this will inform the physician that the patient is becoming less active. Accordingly, the physician may consider it necessary to change the patient's therapy. Thus, by virtue of the present invention, the physician will have important trend data not previously available for diagnosis and follow-up.

In addition to providing valuable trend data, the implantable device of the present invention, when in the form of a cardiac rhythm management device of the type illustrated in FIG. 1, may itself automatically adjust pacing therapy responsive to the physiological parameter measurements. For example, the processor 60 may be programmed to assess the heart sound values at pre-set intervals, such as each night. If the heart sounds (either amplitude or time intervals) are below a predetermined value, indicating an accumulation of fluid in the patient's lungs, the processor may then increase the pacing rate as the patient sleeps. This will assist the body in removing the fluid from the lungs.

Thus, an implantable cardiac device and method for detecting a progression or regression in heart disease over an extended time period and adapting cardiac rhythm management therapy are provided. One skilled in the art will appreciate that the present invention can be practiced by other than the described embodiments, which are presented for the purposes of illustration and not of limitation, and the present invention is limited only by the claims that follow.

What is claimed is:

1. In an implantable cardiac stimulation device, a system for monitoring a progression and regression of a patient's heart disease, the system comprising:

a sensing circuit that senses a patient's cardiac signals;

an acoustic sensor that detects a patient's heart sounds;

a processor programmed to determine relative changes in at least one heart sound, and to provide information related to the relative changes indicating whether there is progression or regression in the patient's heart disease;

timing circuitry, coupled to the sensing circuit and the acoustic sensor, that is operative to determine a time interval between a selected heart sound and a selected cardiac event within the patient's cardiac signals; and wherein the processor is programmed to determine relative changes in the time interval between the selected heart sound and the selected cardiac event within the patient's cardiac signal, the processor further being programmed to detect a progression of heart disease based on the relative changes in the time interval.

2. The system of claim 1, further comprising:

timing circuitry, coupled to the sensing circuit and the acoustic sensor, for determining a time interval between a selected heart sound and a selected cardiac event within the patient's cardiac signals; and wherein the processor is programmed to determine relative changes in the time interval between the selected heart sound and the selected cardiac event within the patient's cardiac signal.

3. The system of claim 2, wherein the selected heart sound is a patient's first heart sound, S1, and the selected cardiac event is an R-wave, so that the time interval corresponds to an interval from each R-wave to the first heart sound following a respective R-wave.

4. The system of claim 1, further comprising:

timing circuitry, coupled to the sensing circuit and the acoustic sensor, for determining a time interval between two heart sounds; and the processor is programmed to determine relative changes in the time interval between the two heart sounds.

5. The system of claim 4, wherein the two heart sounds correspond to a first heart sound, S1, and a second heart sound, S2.

6. The system of claim 1, further comprising:

detecting circuitry, coupled to the acoustic sensor, for determining the absence or presence of selected heart sounds; and wherein the processor is programmed to detect relative changes in the absence or presence of selected heart sounds.

7. The system of claim 1, further comprising:

amplitude detecting circuitry, coupled to the acoustic sensor, for determining the amplitude of selected heart sounds; and wherein the processor is programmed to detect relative changes in the amplitude of selected heart sounds.

8. The system of claim 1, further comprising:

a pulse generator for generating stimulation pulse therapy; and wherein the processor is programmed to adjust the stimulation pulse therapy in response to the relative changes in the at least one heart sound to improve hemodynamics.

9. The system of claim 1, wherein the processor is programmed to determine the relative changes in the at least one heart sound during a predetermined time period each day.

10. The system of claim 1, further comprising:

an activity detector that detects activity of the patient; and wherein the processor determines the relative changes in the at least one heart sound while the patient is inactive.

11. The system of claim 1, wherein the processor is further programmed to average the relative changes in the at least one heart sound over a predetermined period of time.

12. The system of claim 6, further comprising:

a memory that stores the relative changes in the at least one heart sound;and a telemetry circuit that transmits the relative changes in the at least one heart sound to an external receiver.

13. In an implantable cardiac stimulation device, a system for monitoring a progression and regression of a patient's heart disease, the system comprising;

sensing means for providing an electrogram signal representing electrical activity of a patient's heart;

sound sensing means for providing a heart sound signal of the patient's heart; and determining means for determining relative changes in at least one heart sound, and to provide information related to the relative changes indicating whether there is progression or regression in the patient's heart disease, wherein the determining means comprises time span determining means for determining time spans between selected heart sounds in the heart sound signal and selected features in the electrogram signal, wherein the determining means further comprises means for detecting a progression of heart disease based on relative changes in the time spans between selected heart sounds in the heart sound signal and selected features in the electrogram signal.

14. The system of claim 13, wherein the determining means comprises:

time span determining means for determining time spans between selected heart sounds in the heart sound signal and selected features in the electrogram signal, relative changes in the time spans over time indicating whether there is a progression or regression in the patient's heart disease.

15. The system of claim 14, wherein the time spans are time spans between each R wave and a first heart sound following a respective R wave for each sensed cardiac cycle of the patient's heart.

16. The system of claim 13, wherein the determining means comprises:
   time span determining means for determining time spans between selected ones of the heart sounds, wherein relative changes in the time spans over time indicates whether there is a progression or regression in the heart disease.

17. The system of claim 16, wherein the time spans comprise time spans between a first heart sound and a second heart sound following the first heart sound for each sensed cardiac cycle of the patient's heart.

18. The system of claim 14, wherein the time span determining means determines the time spans for cardiac cycles of the patient's heart sensed during a fixed time period each day.

19. The system of claim 14, further comprising:
   activity detecting means for detecting activity of the patient; and
   wherein the time span determining means determines the time spans for heart sounds and electrogram features sensed while the patient is inactive.

20. The system of claim 13, further comprising:
   storing means for storing the relative changes in the at least one heart sound; and
   telemetry means for conveying the relative changes to the at least one heart sound to an external receiver.

21. The system of claim 13, wherein a healthy patient is defined as having at least a first and a second heart sound, and a patient with congestive heart disease, CHF, is defined as having at least one of a third or fourth heart sound, further comprising:
   means for determining the absence or presence of the patient's third and fourth heart sounds; and
   wherein the determining means determines relative changes in the absence or presence of selected heart sounds so as to detect whether a patient has developed CHF.

22. The system of claim 13, further comprising:
   amplitude detecting means, coupled to the sound sensing means, for determining the amplitude of selected heart sounds; and
   wherein the determining means determines relative changes in the amplitude of selected heart sounds and correlate these changes to healthy patients or heart disease patients.

23. The system of claim 13, further comprising:
   pulse generating means for generating stimulation pulse therapy; and
   wherein the determining means further includes means for adjusting the stimulation pulse therapy in response to the relative changes in the at least one heart sound to improve hemodynamics in patients who have heart disease.

24. In an implantable cardiac stimulation device, a method of monitoring a progression or regression of a patient's heart disease, the method comprising the steps of:
   sensing electrical activity of a patient's heart to provide an electrogram signal;
   sensing emitted sounds of the patient's heart to provide a heart sound signal including at least one of a first heart sound, S1, a second heart sound, S2, a third heart sound, S3, and a fourth heart sound, S4;
   processing the electrogram and the heart sound signals to determine relative changes in a predetermined characteristic of selected heart sounds, the predetermined characteristic being selected from at least one of first time duration between an R-wave and S1, second time duration between S1 and S2, and a third time duration between S2 and S1;
   detecting a progression of heart disease based on a change in the selected time duration; and
   providing information related to the relative changes in at least one of such characteristics to indicate whether a there is a progression or regression in the patient's heart disease.

25. The method of claim 24, further comprising the step of averaging the predetermined heart sound characteristic.

26. The method of claim 24, wherein the processing step includes determining the predetermined heart sound characteristic during a predetermined time period each day.

27. The method of claim 24, further comprising the step of communicating the predetermined heart sound characteristic on an external receiver for display thereon.

28. The method of claim 24, further comprising the step of detecting activity of the patient and wherein the predetermined heart sound characteristics are sensed while the patient is inactive.

29. In an implantable cardiac stimulation device, a system for monitoring a progression and regression of heart disease in a patient's heart, the system comprising:
   an acoustic sensor that detects heart sounds;
   a control circuit, coupled to the acoustic sensor, configured to determine relative changes in at least one heart sound over an extended period of time, the control circuit providing an indication that such relative changes over the extended period of time indicates one of the progression or regression in the patient's heart disease;
   a sensing circuit, coupled to the control circuit, that senses R-waves;
   detection circuitry, coupled to the acoustic sensor and the sensing circuit, that discriminates between one or more of a first heart sound, S1, a second heart sound, S2, a third heart sound, S3, a fourth heart sound, S4, and a respective R-wave;
   timing circuitry, coupled to the detection circuitry and the control circuit, that determines a temporal relationship between one or more of the first heart sound, the second heart sound, the third heart sound, the fourth heart sound, and the respective R-wave; and
   wherein the processor is programmed to determine relative changes in one or more of the temporal relationships and to detect a progression of heart disease based on the relative changes in one or more of the temporal relationships.

30. The system of claim 29, further comprising:
   a memory, coupled to the control circuit, that stores the relative changes in the at least one heart sound over the extended period of time; and
   a telemetry circuit, coupled to the memory and the control circuit, that transmits the relative changes in the at least one heart sound to an external receiver that displays the relative changes over the extended period of time.

31. The system of claim 29, further comprising:
   a sensing circuit, coupled to the control circuit, that senses R-waves;
   detection circuitry, coupled to the acoustic sensor and the sensing circuit, that discriminates between one or more of a first heart sound, S1, a second heart sound, S2, a third heart sound, S3, a fourth heart sound, S4, and a respective R-wave; and timing circuitry, coupled to the detection circuitry and the control circuit, that determines a temporal relationship between one or more of the first heart sound, the second heart sound, the third heart sound, the fourth heart sound, and the respective R-wave; and wherein the control circuitry is programmed to determine relative changes in one or more of the temporal relationships.

32. The system of claim 29, further comprising:

amplitude measuring circuitry, coupled to the acoustic sensor, that measures the amplitude of selected heart sounds; and wherein the control circuitry is programmed to detect relative changes in the amplitude of selected heart sounds.

33. The system of claim 29, further comprising:

an activity detector that detects activity level of the patient; and wherein the control circuitry determines the relative changes in the at least one heart sound while the patient is inactive.

34. The system of claim 33, wherein the control circuit is further configured to average the relative changes in the at least one heart sound over a predetermined period of time while the patient is inactive.

35. The system of claim 29, further comprising:

a pulse generator, coupled to the control circuit, that generates stimulation pulse therapy; and wherein the control circuit is configured to adjust the stimulation pulse rate in response to a trend in the relative changes in the at least one heart sound to improve hemodynamics.

36. In an implantable cardiac stimulation device, a system for monitoring a progression and regression of a patient's heart disease, the system comprising:

an acoustic sensor that detects heart sounds;

a control circuit, coupled to the acoustic sensor, configured to determine a plurality of relative changes in at least one heart sound, and to provide trend data as to whether there is progression or regression in the patient's heart disease;

a sensing circuit that senses selected cardiac events;

timing circuitry, coupled to the sensing circuit, the control circuit and the acoustic sensor, that determines a time interval between a selected heart sound and a selected cardiac event; and wherein the control circuit is configured to provide the trend data of the relative changes in the time interval between the selected heart sound and the selected cardiac event and to detect a progression of heart disease based on the relative changes in the time interval between the selected heart sound and the selected cardiac event.

37. The system of claim 36, further comprising:

a sensing circuit that senses selected cardiac events;

timing circuitry, coupled to the sensing circuit, the control circuit and the acoustic sensor, that determines a time interval between a selected heart sound and a selected cardiac event; and wherein the control circuit is configured to provide the trend data of the relative changes in the time interval between the selected heart sound and the selected cardiac event.

38. The system of claim 36, further comprising:

timing circuitry, coupled to the control circuit and the acoustic sensor, that determines a time interval between two heart sounds; and the control circuit is configured to provide the trend data of the relative changes in the time interval between the two heart sounds.

39. The system of claim 36, further comprising:

detecting circuitry, coupled to the control circuit and the acoustic sensor, that determines the absence or presence of selected heart sounds; and wherein the control circuit is configured to provide the trend data of the relative changes in the absence or presence of selected heart sounds.

40. The system of claim 36, further comprising:

amplitude detecting circuitry, coupled to the control circuit and the acoustic sensor, that determines the amplitude of selected heart sounds; and wherein the control circuit is configured to detect relative changes in the amplitude of selected heart sounds.

41. The system of claim 36, further comprising:

a pulse generator that generates stimulation pulse therapy; and wherein the control circuit is configured to increase the stimulation pulse rate in response to a determination of the progression of heart disease to improve hemodynamics.

* * * * *